(12) United States Patent
Chang et al.

(10) Patent No.: US 7,959,600 B2
(45) Date of Patent: Jun. 14, 2011

(54) CONTAINER CLOSURE DELIVERY SYSTEM

(75) Inventors: Byeong Seon Chang, Thousand Oaks, CA (US); Roger Wongjung Liu, Moorpark, CA (US)

(73) Assignee: Byeong S. Chang, Camerillo, CA (US)

( * ) Notice: Subject to any disclaimer, the term of this patent is extended or adjusted under 35 U.S.C. 154(b) by 304 days.

(21) Appl. No.: 11/716,223

(22) Filed: Mar. 9, 2007

(65) Prior Publication Data

US 2007/0225640 A1 Sep. 27, 2007

Related U.S. Application Data

(63) Continuation-in-part of application No. 11/172,064, filed on Jun. 30, 2005.

(60) Provisional application No. 60/640,625, filed on Dec. 30, 2004.

(51) Int. Cl.
*A61M 37/00* (2006.01)
(52) U.S. Cl. .................. 604/89; 604/82; 604/92
(58) Field of Classification Search .............. 604/92, 604/518, 533, 82–91
See application file for complete search history.

(56) References Cited

U.S. PATENT DOCUMENTS

| | | | |
|---|---|---|---|
| 3,330,280 A * | 7/1967 | Ogle ..................... 604/89 |
| 3,342,180 A * | 9/1967 | Sandhage et al. ........... 604/89 |
| 3,678,931 A | 7/1972 | Cohen |
| 3,685,514 A | 8/1972 | Cheney |
| 3,739,947 A | 6/1973 | Baumann et al. |
| 3,766,917 A | 10/1973 | Wimmer |
| 3,826,260 A | 7/1974 | Killinger |
| 3,838,689 A | 10/1974 | Cohen |
| 4,153,186 A | 5/1979 | Nye |
| 4,172,457 A | 10/1979 | Choksi et al. |
| 4,328,802 A | 5/1982 | Curley et al. |
| 4,410,321 A | 10/1983 | Pearson et al. |
| 4,411,662 A | 10/1983 | Pearson |
| 4,432,755 A | 2/1984 | Pearson |
| 4,458,733 A | 7/1984 | Lyons |
| 4,610,669 A * | 9/1986 | Meyer et al. ........... 604/218 |
| 4,872,867 A | 10/1989 | Joh |
| 4,886,495 A * | 12/1989 | Reynolds ............... 604/88 |
| 4,898,209 A | 2/1990 | Zbed |
| 5,080,649 A | 1/1992 | Vetter |
| 5,435,076 A | 7/1995 | Hjertman et al. |
| 5,472,422 A | 12/1995 | Ljungquist |
| 5,489,266 A | 2/1996 | Grimard |
| 5,549,561 A | 8/1996 | Hjertman |
| 5,569,193 A | 10/1996 | Hofstetter et al. |
| 5,685,846 A | 11/1997 | Michaels, Jr. |
| 5,716,339 A | 2/1998 | Tanaka et al. |
| 5,752,940 A | 5/1998 | Grimard |
| 5,779,668 A | 7/1998 | Grabenkort |
| 5,817,055 A | 10/1998 | Ljungquist |
| 5,833,653 A | 11/1998 | Vetter et al. |
| 5,876,372 A | 3/1999 | Grabenkort et al. |
| 6,149,628 A | 11/2000 | Szapiro et al. |
| 6,152,897 A | 11/2000 | Limrell et al. |
| 6,319,225 B1 | 11/2001 | Sugita et al. |

(Continued)

*Primary Examiner* — Nicholas D Lucchesi
*Assistant Examiner* — Rebecca E Eisenberg

(57) ABSTRACT

A container closure delivery system that is suitable for lyophilized pharmaceutical injectable powder products is disclosed. The system comprises storage stable powder formulations and a container closure assembly design wherein the formulation can be filled and lyophilized with a standard fill finish equipment, and the formulations and lyophilization processes are optimized to produce a powder that readily dissolves upon contact with a diluent, thereby facilitating the direct injection of the lyophilized product without the need for a separate reconstitution/mixing/priming step.

2 Claims, 11 Drawing Sheets

U.S. PATENT DOCUMENTS

| | | |
|---|---|---|
| 6,386,872 B1 | 5/2002 | Mukasa et al. |
| 6,406,455 B1 | 6/2002 | Willis et al. |
| 6,419,656 B1 | 7/2002 | Vetter et al. |
| 6,440,101 B1 | 8/2002 | Grabenkort et al. |
| 6,514,231 B1 | 2/2003 | Szapiro et al. |
| 6,547,755 B1 | 4/2003 | Lippe et al. |
| 6,692,468 B1 | 2/2004 | Waldenburg |
| 6,752,292 B2 * | 6/2004 | Van Herpen .................. 222/137 |
| 6,817,987 B2 | 11/2004 | Vetter et al. |
| 6,846,300 B2 | 1/2005 | Horth et al. |
| 6,852,103 B2 | 2/2005 | Fowles et al. |
| 6,902,543 B1 | 6/2005 | Cherif-Cheikh et al. |
| 2002/0068896 A1 | 6/2002 | Robinson et al. |
| 2003/0176834 A1 * | 9/2003 | Horth et al. ..................... 604/85 |
| 2005/0096588 A1 | 5/2005 | Hagmann et al. |
| 2005/0263615 A1 | 12/2005 | Kriesel et al. |
| 2006/0100587 A1 | 5/2006 | Bertron et al. |
| 2008/0195082 A1 * | 8/2008 | Pauser et al. .................. 604/518 |

* cited by examiner

CONTAINER CLOSURE DELIVERY SYSTEM

RELATED PATENT APPLICATIONS

This application is a continuation-in-part application of U.S. patent application Ser. No. 11/172,064, filed on Jun. 30, 2005, which claims the benefit of U.S. Provisional Application No. 60/640,625, filed on Dec. 30, 2004, each incorporated in its entirety by reference herein.

TECHNICAL FIELD

The field of the present invention is a container closure delivery system that is suitable for lyophilized pharmaceutical injectable products and which facilitates the easy, direct injection of the lyophilized product without the need for a reconstitution/mixing step of the powder and a liquid diluent.

BACKGROUND OF THE INVENTION

Due to continued advances in genetic and cell engineering technologies, proteins known to exhibit various pharmacological actions in vivo are capable of production in large amounts for pharmaceutical applications. However, one of the most challenging tasks in the development of protein pharmaceuticals is to deal with the inherent physical and chemical instabilities of such proteins, especially in aqueous dosage forms. To try to understand and maximize the stability of protein pharmaceuticals and any other usable proteins, many studies have been conducted, especially in the past two decades. These studies have covered many areas, including protein folding and unfolding/denaturation, mechanisms of chemical and physical instabilities of proteins, as well as various means of stabilizing proteins in aqueous form; see, e.g., Manning et al., Pharm. Res., 1989; 6:903-918; Arakawa et al., Adv Drug Deliv Rev., 2001; 46:307-326; Wang W., Int J Pharm., 1999; 185:129-188; Chen T., Drug Dev Ind Pharm., 1992; 18:1311-1354, and references cited therein.

Because of the instability issues associated with the aqueous dosage forms, powder formulations are generally preferred to achieve sufficient stability for the desired shelf life of the product. Various techniques to prepare dry powders have been known, substantiated and practiced in the pharmaceutical and biotech industry. Such techniques include lyophilization, spray-drying, spray-freeze drying, bulk crystallization, vacuum drying, and foam drying. Lyophilization (freeze-drying) is often a preferred method used to prepare dry powders (lyophilizates) containing proteins. Various methods of lyophilization are well known to those skilled in the art; see, e.g., Pikal M J., In: Cleland J L, Langer R. eds. Formulation and Delivery of Proteins and Peptides. Washington, D.C.: American Chemical Society; 1994:120-133; Wang W., Int J Pharm. 2000; 203:1-60, and references cited therein.

The lyophilization process consists if three stages: freezing, primary drying, and secondary drying. Because the protein product is maintained frozen throughout drying process, lyophilization provides the following advantages over alternative techniques: minimum damage and loss of activity in delicate, heat-liable materials; speed and completeness of rehydration; the possibility of accurate, clean dosing into final product containers so that particulate and bacterial contamination is reduced; permits product reconstitution at a higher concentration than it was at the time of freezing; and permits storage of the product at ambient temperatures. The latter can be particularly useful for hospital products in areas that do not have ready access to freezers, especially ultra-cold freezers.

Unfortunately, even in solid dosage forms, some proteins can be relatively unstable and this instability may be a product of the lyophilization method used for preparing the solid dosage forms and/or the inherent instability of the actual solid dosage formulations themselves. For example, in certain instances, lyophilization processing events can force a protein to undergo significant chemical and physical changes. Such processing events include concentration of salts, precipitation, crystallization, chemical reactions, shear, pH, amount of residual moisture remaining after freeze-drying, and the like. Such chemical and physical changes include, e.g., formation of dimer or other higher order aggregates, and unfolding of tertiary structure. Unfortunately, these changes may result in loss of activity of the protein, or may result in significant portions of the active materials in the drug having been chemically transformed into a degradation product or products which may actually comprise an antagonist for the drug or which may give rise to adverse side effects. In addition to the instabilities incurred upon proteins because of the inherent steps of the lyophilization process, other disadvantages of lyophilization include: long and complex processing times; high energy costs; and expensive set up and maintenance of the lyophilization facilities. As such, use of lyophilization is usually restricted to delicate, heat-sensitive materials of high value. Additionally, lyophilized powders are typically formed as cakes, which require additional grinding and milling and optionally sieving processing steps to provide flowing powders. To try to understand and to optimize protein stability during lyophilization and after lyophilization, many studies have been conducted; see, e.g., Gomez G. et al., Pharm Res. 2001; 18:90-97; Strambini G B., Gabellieri E., Biophys J., 1996; 70:971-976; Chang B S. et al., J Pharm Sci., 1996; 85:1325-1330, Pikal M J., Biopharm, 1990; 3:9, Izutsu K. et al., Pharm. Res., 1994; 11-995, Overcashier D E., J Pharm Sci., 1999; 88:688, Schmidt E A. et al., J Pharm Sci., 1999; 88:291, and references cited therein.

In order to allow for parenteral administration of these powdered drugs, the drugs must first be placed in liquid form. To this end, the drugs are mixed or reconstituted with a diluent before being delivered parenterally to a patient. The reconstitution procedure must be performed under sterile conditions, and in some procedures for reconstituting, maintaining sterile conditions is difficult. One way of reconstituting a powdered drug is to inject a liquid diluent directly into a drug vial containing the powdered drug. This can be performed by use of a combination-syringe and syringe needle having diluent contained therein and drug vials which include a pierceable rubber stopper. The method of administration goes as follows: 1) the rubber stopper of the drug vial is pierced by the needle and the liquid in the syringe injected into the vial; 2) the vial is shaken to mix the powdered drug with the liquid; 3) after the liquid and drug are thoroughly mixed, a measured amount of the reconstituted drug is then drawn into the syringe; 4) the syringe is then withdrawn from the vial and the drug then be injected into the patient.

For people requiring frequent parenteral administration of drugs, it is common practice for those people to be provided with home-use kits which may include injection cartridges, pre-filled syringes, pen injectors and/or autoinjectors to be used for the purpose of self-administration. Autoinjectors incorporating needled injection mechanisms are well known and thought to exhibit several advantages relative to simple hypodermic syringes. Such needled autoinjectors generally include a body or housing, a needled syringe or similar device, and one or more drive mechanisms for inserting a needle into the tissue of the subject and delivering a desired dose of liquid medicament through the inserted needle. To date, all known autoinjector devices have been used with liquid formulations. There still exists a need for an autoinjector that can used to deliver powdered formulations.

Other methods of administration of powdered drugs include the use of dual-chambered injection cartridges and/or pre-filled syringe systems. Injection cartridges of the dual-chamber type are well-known and have found a wide use. They are used together with various types of injection apparatuses which serve to hold the cartridge as it is readied for injection and as injections are subsequently administered. Injection cartridges of the dual-chamber type generally comprise a cylindrical barrel, which is shaped like a bottleneck at its front end and has an open rear end. The front end is closed by a septum of rubber or other suitable material, which is secured in place by means of a capsule. This capsule has a central opening where the septum is exposed and may be pierced by a hollow needle to establish a connection with the interior of the cartridge; see e.g., U.S. Pat. No. 5,435,076 and references cited therein.

Dual-chambered pre-filled syringe systems are well known and have found wide commercial use; see e.g., U.S. Pat. Nos. 5,080,649; 5,833,653; 6,419,656; 5,817,056; 5,489,266, and references cited therein. Pre-filled syringes of the dual-chambered type generally comprise an active ingredient which is lyophilized in one chamber, while a second chamber of the syringe contains a solvent that is mixed with the active substance immediately before application. In such devices, in order to facilitate the movement of the syringe plunger against compression of air, the chamber containing the lyophilized product typically has large head space and some additional mechanism, e.g., rotation of the plunger, screwing in the plunger, is necessary. As a result, the reconstituted drug needs to primed to remove large volumes of air prior to injection; see e.g., U.S. Pat. No. 6,817,987 which describes a hypodermic syringe which holds a solvent and a soluble component (medicament) and wherein the solvent and medicament are mixed as the user presses and then releases the plunger of the syringe. Upon complete mixing, the user attaches a needle and then rotates the plunger of the syringe to allow for the injection.

Several syringe devices of various configurations and various processes of lyophilization have been described in, e.g., U.S. Pat. Nos. 5,752,940; 5,876,372; 6,149,628; 6,440,101, and references cited therein. Importantly, in each instance, the devices comprise multiple parts and require at least a two step, two directional reconstitution process for the delivery of the lyophilized powdered drug. Other devices used for reconstitution and delivery of powdered drugs are described in, e.g., U.S. Pat. Nos. 4,328,802; 4,410,321; 4,411,662; 4,432,755; 4,458,733; 4,898,209; 4,872,867; 3,826,260, and references cited therein.

Unfortunately, because all of these known methods require thorough reconstitution/mixing of the lyophilized product into the diluent prior to injection, they can typically involve lengthy procedures (in excess of 10 steps) in order to reconstitute the solid drug into a liquid formulation prior to administration. Such lengthy reconstitution steps can be complex, arduous and tedious for the patient and may render injection of the lyophilized product unfeasible. Moreover, these complicated procedures present risks of foaming, risk of contamination, and risk of accidental needle pricks. There clearly still exists a need for improved delivery devices and methods.

Co-pending U.S. patent application Ser. No. 11/172,064 ('064) provides an advancement in the technology and relates to a container closure assembly suitable for lyophilized pharmaceutical injectable products and designed to provide for direct injection of a lyophilized product without the need for a reconstitution/mixing/priming step of the powder and diluent prior to injection. The components of the disclosed container closure assembly were designed to function in a manufacturing function and an end user function and, upon completion of the lyophilization process, the assembly has minimal head space to avoid the need for priming. The disclosed container closure assembly is designed to utilize or be easily adaptable to industry standard or existing filling systems, thus providing a more economical alternative to prior art devices.

The present invention provides an improved alternative container closure design which facilitates the easy, direct injection of the lyophilized product without the need for a reconstitution/mixing/priming step of the powder and a liquid diluent by the end user. As with the assemblies described in the '064 application, the disclosed container closure assembly is designed to utilize or be easily adaptable to industry standard or existing filling systems, thus providing a more economical alternative to prior art devices.

SUMMARY OF THE INVENTION

The container closure assembly of the present invention consists of three operating components designed to function in a manufacturing function and an end user function: a plug component; a top cup component; and a product container component. The plug component and top cup component are specifically designed to snugly engage with each other to form a plunger assembly that can then be inserted into the product container. Alternatively, the plunger assembly may be a one piece component comprising specific features the top cup component and plug component. The plunger assembly may thus vary in size and configuration and have varying manufacturing and/or end user functionality. The product container component is specifically designed to hold a liquid to be lyophilized and capable of holding a plunger assembly. The product container may vary in size and configuration but is typically cylindrical in shape, and has at one end an opening and at the opposing end an ejection port. An important, unique design feature of the product container is a spiral mixing channel that is integrated into the product container at the lower base and which serves to improve product yield.

Importantly, the container closure assembly of the present invention is designed to utilize or be easily adaptable to industry standard or existing lyophilization systems, thus providing an economical alternative. Upon completion of the lyophilization process, the plunger assembly is compressed such that it compresses the powdered pharmaceutical product, i.e., there is minimum head space between the product container and the plunger assembly, and the plunger assembly serves as a path to allow for the flow of liquid into the container closure assembly, i.e., allow for liquid to encounter the powder and rapidly reconstitute without the need for priming. Because of the unique assembly design, the container closure assembly facilitates the easy, direct injection of the lyophilized product without the need for a reconstitution/mixing/priming step of the powder and a liquid diluent by the end user.

Another object of the present invention is an improved process for the preparation of a container closure assembly containing a lyophilized powder product. This improved process comprises the following steps: 1) utilizing an industry standard vial manufacturing filling line, the product container is loaded into the equipment in a similar manner as regular vials; 2) the product container is filled with liquid active ingredient; 3) a plunger assembly is dropped into an "open" position on top of the product container, engaged with the product container in the same manner as lyophilization stoppers are mounted to regular vials; 4) the complete container closure assembly is then placed into the lyophilizer; 5) upon lyophilization, vapor is allowed to escape via the openings between the plunger assembly and product container; 6) upon completion of lyophilization, vertical compression of the lyophilizer shelves will seal the plunger assembly into the product container with minimal head space; and 7) the sealed container closure assembly is bonded to provide a tamper resistant assembly which retains the sterility of the active ingredient.

Another object of the present invention is an improved method for the administration of a lyophilized pharmaceutical powder product using the container closure system of the present invention. In one embodiment, this improved method of administration comprises the following steps: 1) a tangential force is applied to the tab seal at the top end of the sealed container closure assembly containing the lyophilized powder product to allow attachment via friction fit to either a luer-lock or luer-slip syringe containing the diluent; 2) the detachable base at the ejection port end of the container closure assembly is detached, thus exposing a tip for the attachment of a standard type needle; 3) a standard type needle is attached to said exposed tip of the container closure assembly; 4) the injection is then initiated as normal by inserting the needle into the injection site; and 5) force is applied to the syringe plunger whereupon the diluent in the syringe will be forced through the container closure assembly, encounter the lyophilized powder and rapidly reconstitute the powder to allow the liquefied product mixture to flow into the injection site, completing the injection. Importantly, there is no requirement for a reconstitution/mixing/priming step of the powder and diluent by the end user.

DETAILED DESCRIPTION OF THE INVENTION

As those in the art will appreciate, the foregoing detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

Figure 1:
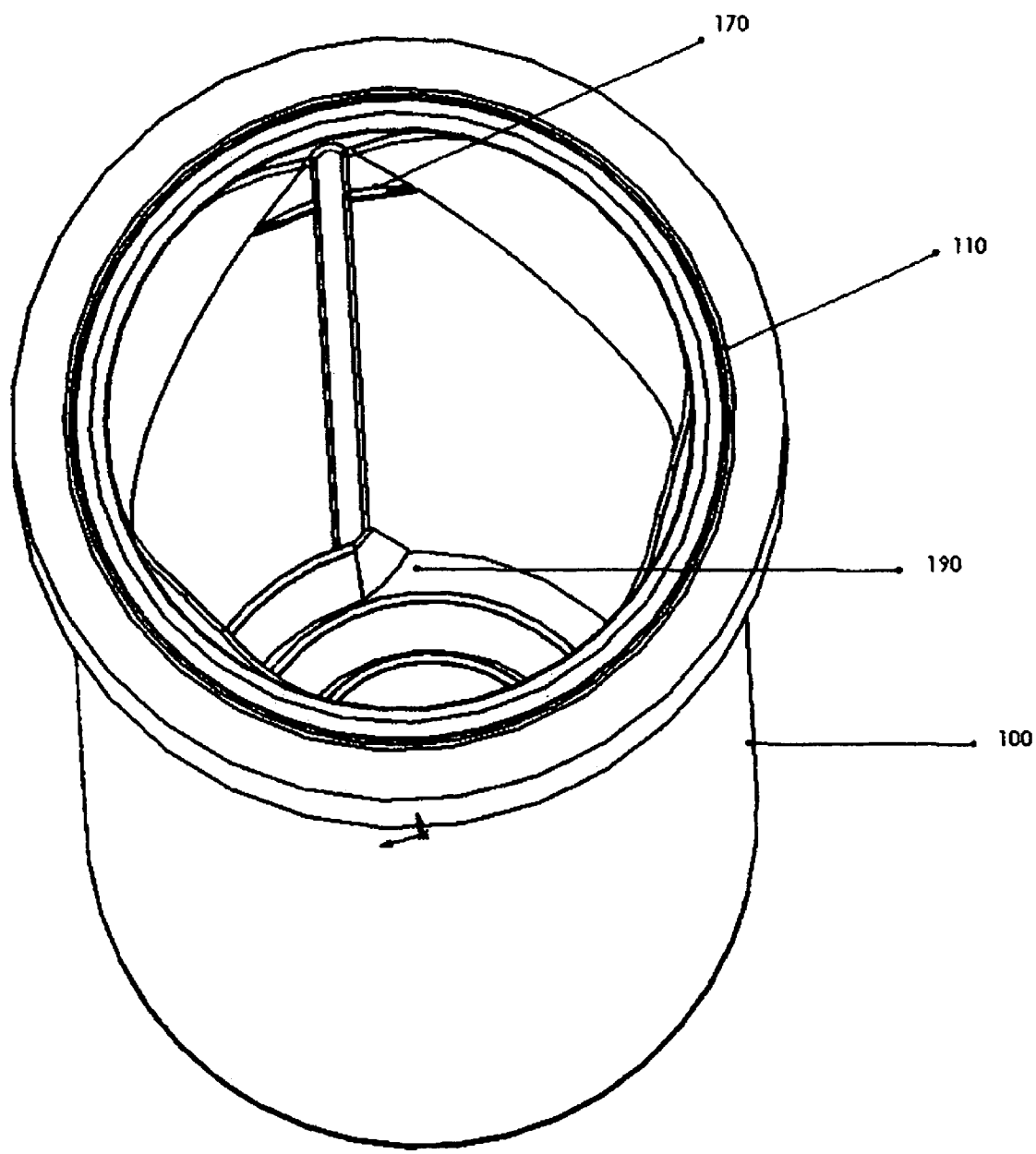
FIG. 1 shows an elevation perspective view from the upper base of a product container contemplated for use in the container closure assembly of the present invention.
Figure 2:
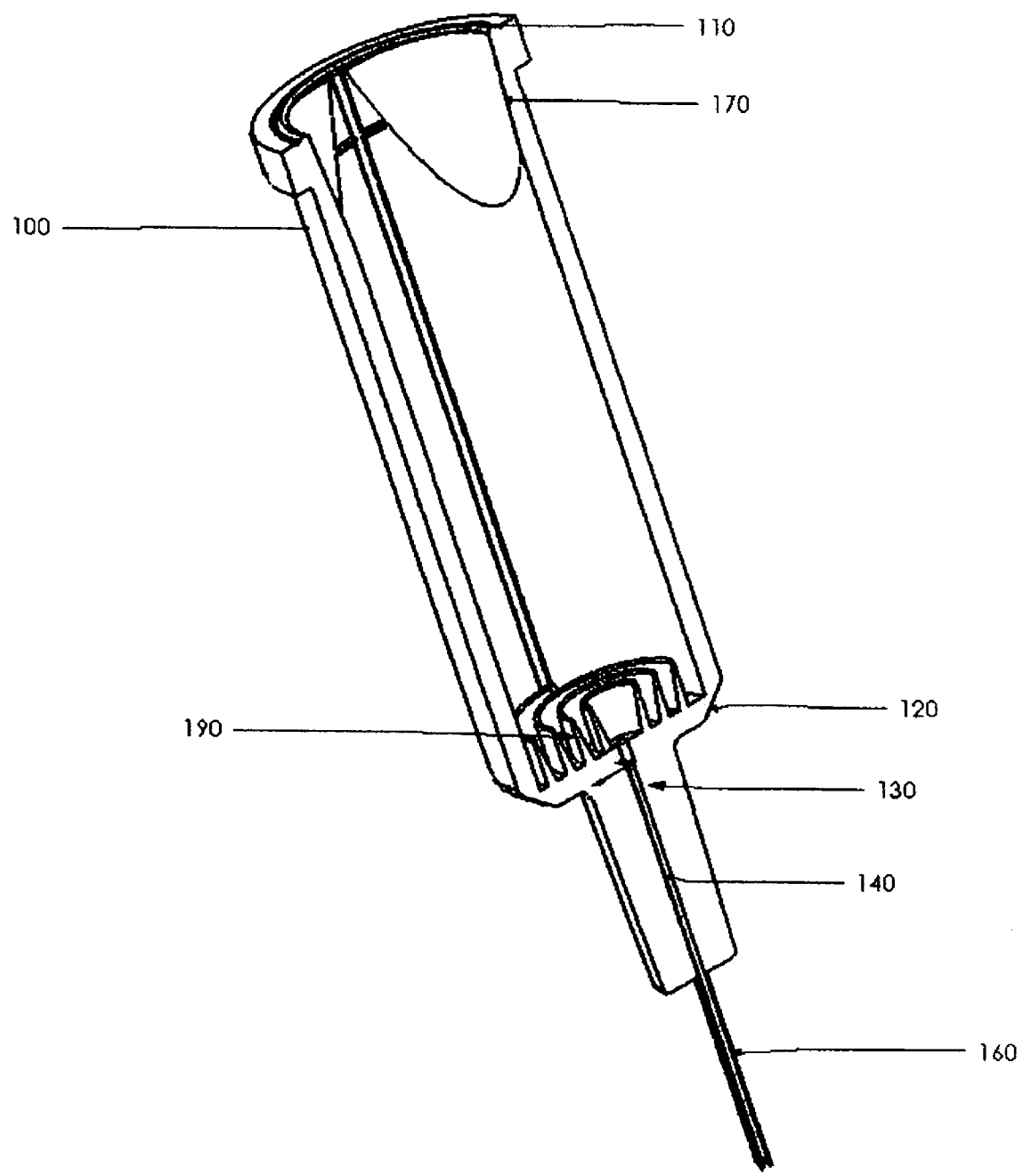
FIG. 2 shows a perspective view of a product container contemplated for use in the container closure assembly of the present invention, shown along a vertical plane.

Referring now in more detail to the drawings, FIGS. 1 and 2 depict the product container 100 of the described container closure assembly 600. The product container 100 is constructed of a suitable plastic material and is cylindrical in shape. The upper base 110 of the product container 100 is completely open. The product container 100 has a hollow circular inside to create sufficient holding volume of liquid active ingredient and specifically designed to accept a plunger assembly 500 which is formed when the top cup component 300 is fully engaged with the plug component 400. The lower base 120 comprises a coaxial hollow ejection port 130 where an internal tube 140 is defined through which the liquid active ingredient flows toward an injection needle. The outer surface area of the ejection port 130 is of a sufficient radius to allow for a friction fit of a standard type luer slip or luer lock syringe needle attachment at the tip of the port. A locking ridge 170 is integrated into the sidewall of the product container 100 such that upon full insertion of the plunger assembly, the plunger assembly cannot be removed. A spiral mixing channel 190 is integrated into the product container at the lower base 120. The product container 100 depicted in FIG. 2 comprises a staked needle 160 at the ejection port 130.

Figure 3:
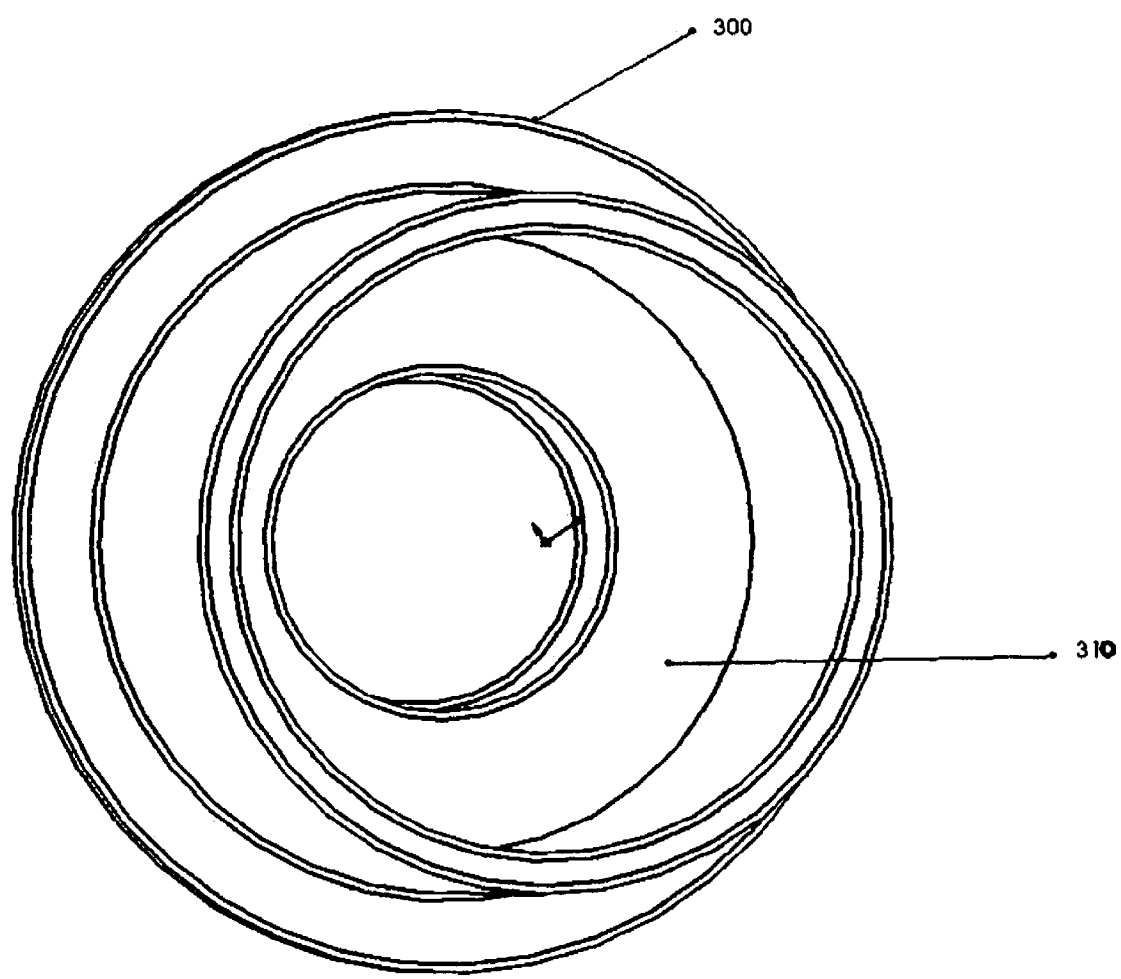
FIG. 3 shows an elevation perspective view from the bottom of a top cup component contemplated for use in the container closure assembly of the present invention.
Figure 4:
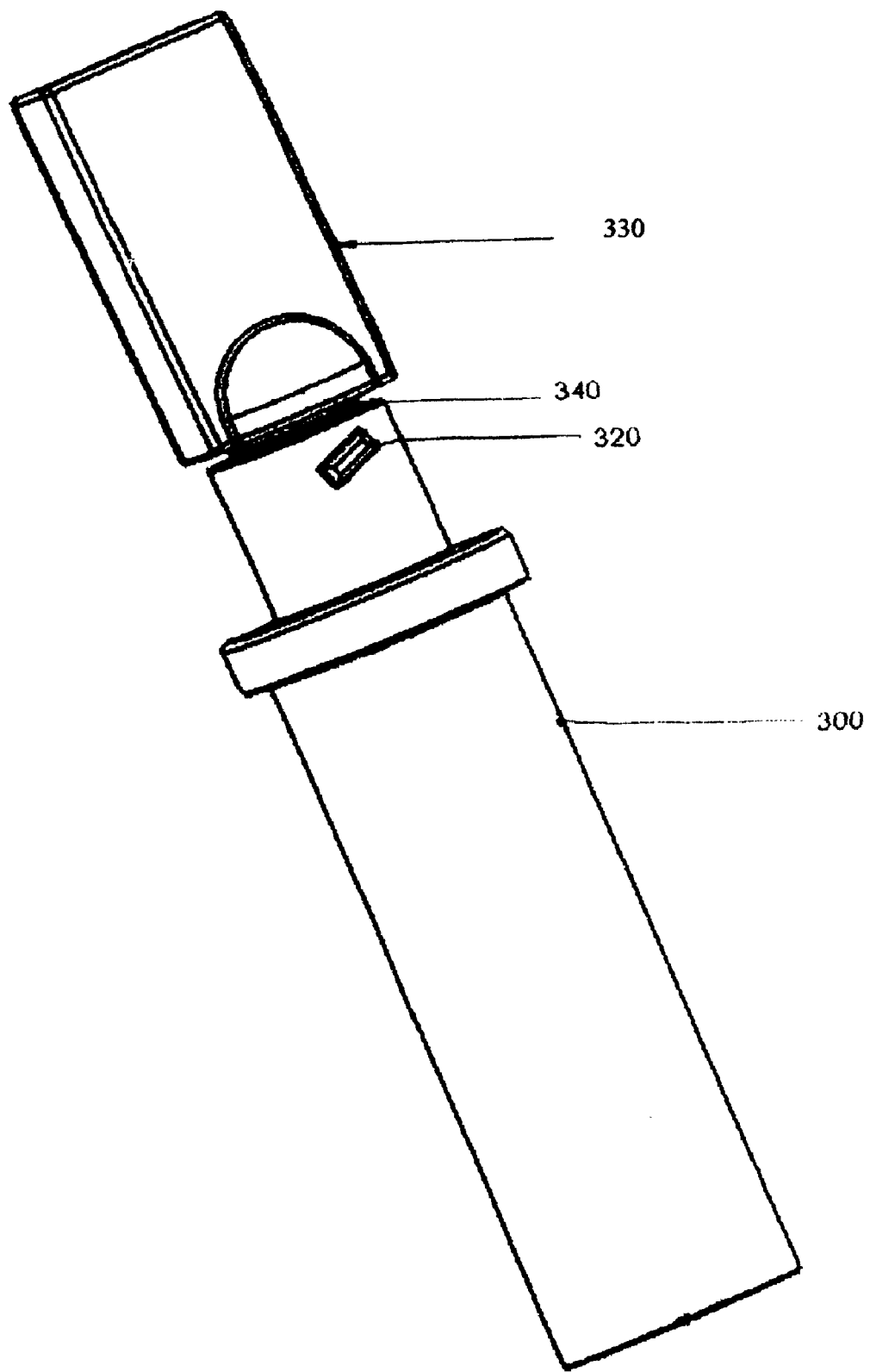
FIG. 4 shows a perspective view of a top cup component contemplated for use in the container closure assembly of the present invention.

FIGS. 3 and 4 depict the top cup component 300 of the described container closure assembly 600. This top cup component 300 is envisaged to be constructed out of a suitable plastic material. The top cup component 300 has a hollow circular inside 310 and is constructed to accept and fully engage with the plug portion 400 to create a plunger assembly 500 for the container closure assembly 600. In FIG. 4, a tab seal 330 is depicted and at the base of the tab seal 330 is a break or scoring point 340 formed such that when the tab seal 330 is torqued, it will break off at this point 340. Upon removal of the tab seal 330, a fluid transfer channel is defined which facilitates the flow of diluent from an attached syringe through the assembled plunger assembly 500 to encounter the lyophilized powder in the product container 100. A luer lock tab 320 is depicted where a standard type luer slip syringe (containing diluent) can be frictionally attached after removal of a tab seal 330 to provide a means to administer reconstituted lyophilized powder to a patient when force is applied to the syringe plunger.

Figure 5:
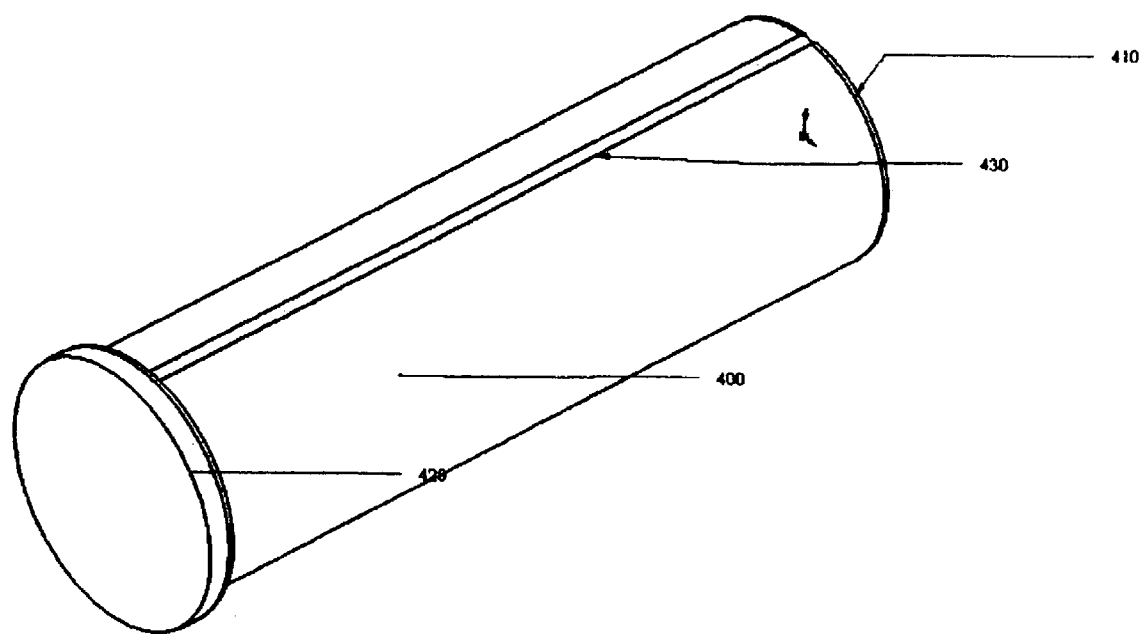
FIG. 5 shows a perspective view of a plug portion contemplated for use in the container closure assembly of the present invention.

FIG. 5 shows the plug component 400 of the described container closure assembly 600. This plug component 400 is envisaged to be constructed of a suitable plastic material and designed to fully engage with the top cup component 300 with a snug fit to form a plunger assembly 500. The proximal end 410 of the plug component 400 is designed such that when fully engaged with the top cup component 300 there is minimal fluid head space, i.e., minimal holdup volume of the transfer diluent. The distal end 420 of the plug component 400 is designed such that when the plunger assembly is fully engaged with the product container 100 the plunger assembly rests directly on top of the powdered active ingredient and there is minimal fluid head space. A fluid transfer channel 430 extending axially from the proximal end to the distal end on the outside of the plug component 400 facilitates the flow of diluent through said plunger assembly 500.

Figure 6:
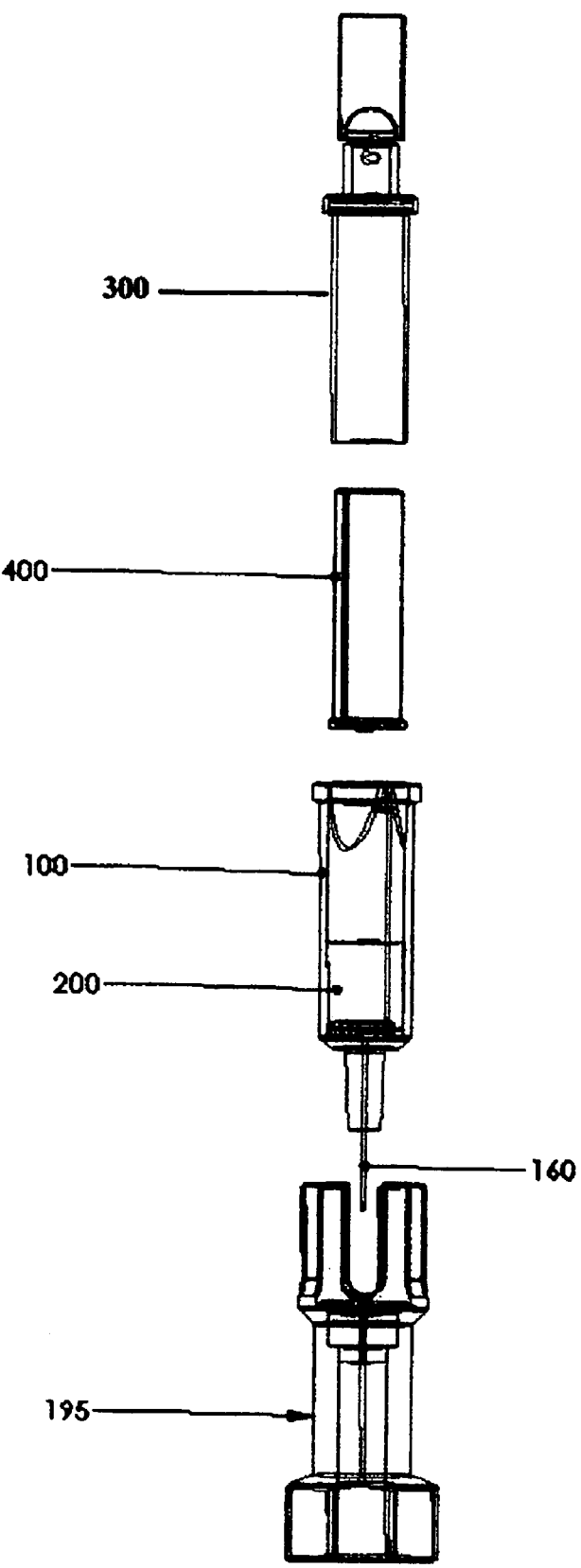
FIG. 6 is a perspective view showing the arrangement of elements and parts for one embodiment of the container closure assembly of the present invention.

FIG. 6 depicts the arrangement of the top cup component 300, the plug portion 400, and the product container 100 (containing liquid active ingredient 200) for one embodiment of the container closure assembly of the present invention prior to being loaded into a industry standard vial/syringe/cartridge manufacturing filling line. In the embodiment depicted in FIG. 6, the product container comprises a staked needle 160 at the ejection port which will be covered by a detachable base 195 which serves as a needle shield.

Figure 7:
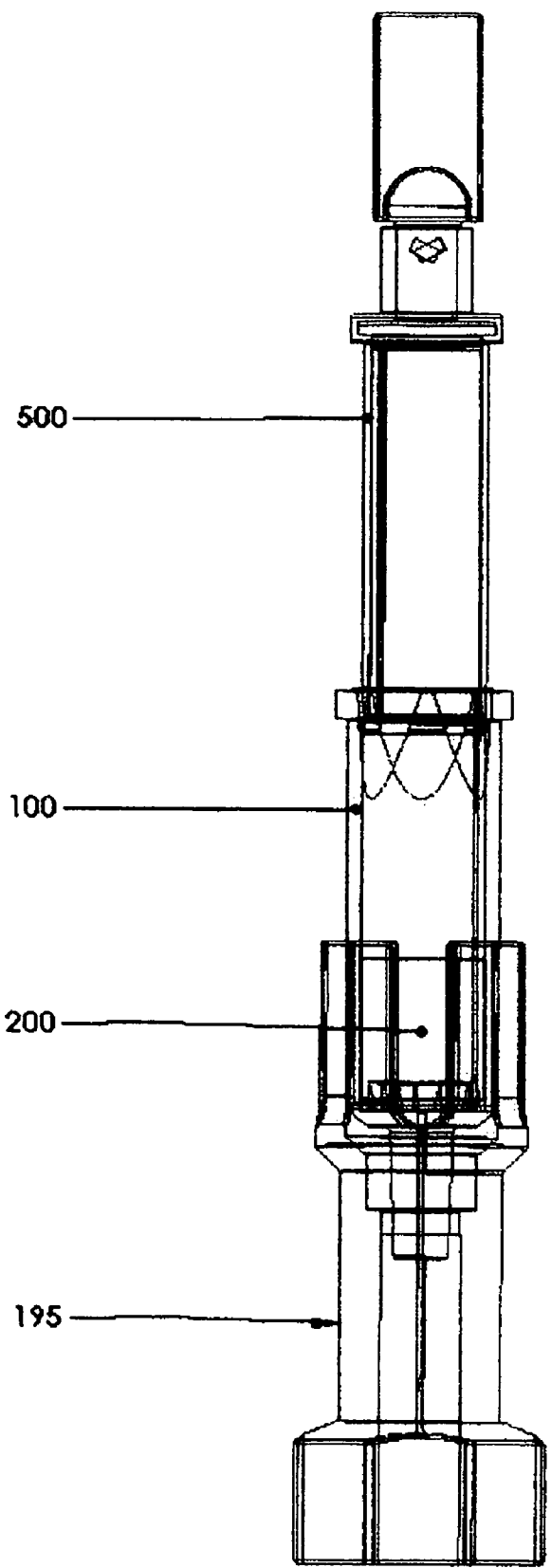
FIG. 7 shows a perspective view of an embodiment of the container closure assembly whereupon a plunger assembly consisting of a top cup component and a plug component are installed upon the product container after the filling the product container with liquid active ingredient and prior to placement of the container closure assembly within a freeze drying apparatus, i.e., the plunger assembly is installed in an "open" position in the product container.

FIG. 7 shows a perspective view of the container closure assembly 600 embodiment of FIG. 6 whereupon the plunger assembly 500 (consisting of a top cup component fully engaged with the plug component) is installed upon the product container 100 after the filling the product container 100 with liquid active ingredient 200 and prior to placement of the container closure assembly within a freeze drying apparatus, i.e., the plunger assembly 500 is installed in an "open" position in the product container 100 and the product container 100 rests in the needle shield/base 195.

Figure 8:
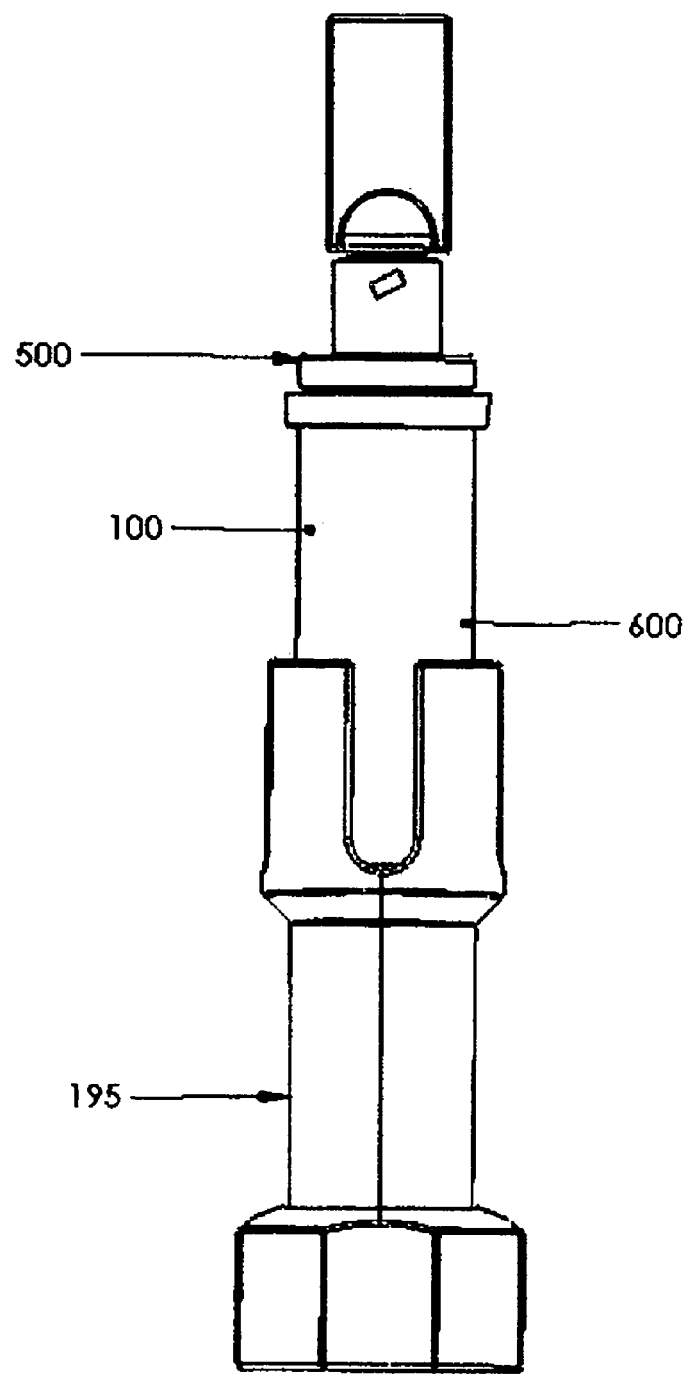
FIG. 8 shows a perspective view of an embodiment of the container closure assembly upon completion of the freeze drying cycle whereupon the liquid active ingredient has formed into a dry powder and the plunger assembly has been compressed by the freeze dryer shelves to create a sealed container closure assembly.

FIG. 8 shows a perspective view of the container closure assembly 600 embodiment of FIG. 7 upon completion of the freeze drying cycle whereupon the liquid active ingredient has formed into a dry powder (not visible) and the plunger assembly 500 has fully engaged with the product container 100 to compress the powdered active ingredient with minimal fluid head space.

Figure 9:
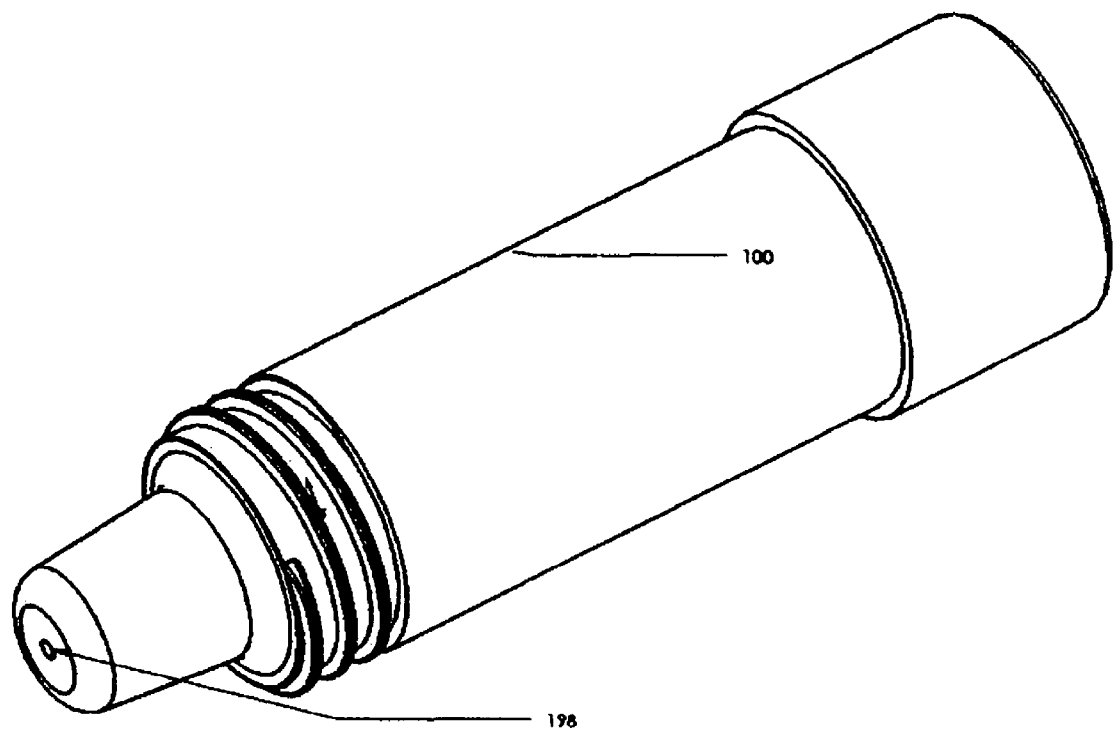
FIG. 9 shows a perspective view of an alternative product container design contemplated for use in the container closure assembly of the present invention, wherein the ejection port of the product container comprises a nozzle spray tip for nasal delivery.

FIG. 9 depicts an alternative product container design contemplated for use in the container closure assembly of the present invention, wherein the ejection port of the product container comprises a nozzle spray tip 198 for nasal delivery.

Contemplated for use in the container closure assembly of the present invention are storage stable powder formulations of pharmaceutical products. Importantly, the powder formulations of the present invention are optimized to produce powders which provide for "rapid" dissolution of the lyophilized powder, i.e., the powders are readily and immediately dissolved upon contact with a liquid diluent. The lyophilized powders of the present invention comprise an active ingredient, e.g., protein, and a stabilizer. Stabilizers are added to the lyophilized formulation to enhance the stability of active ingredient. Stabilizers such as, e.g., surfactants, sugars, polymers, antioxidants, amino acids, salts, can be added to stabilize active ingredient during freezing process; and additives that can replace hydrogen bonds of water during dehydration process, e.g., sucrose, trehalose, lactose, or other sugars, can be added to stabilize pharmaceuticals by maintaining their native structure.

In order to maintain large surface area, the powder formulations may further comprise bulking agents that can form crystalline matrices (e.g., mannitol, glycine, polyethylene glycol, and the like). Alternatively, other glassy bulking agents like sugars and polymers, e.g., sucrose, trehalose, lactose, proteins, dextran and its derivatives, cyclodextran, carboxymethylcellulose, PVA, PVC, starch and its derivatives, can be added to the formulation.

The powder formulations may further comprise surfactants and buffers. Such surfactants include polysorbate 80 (or Tween 80), polysorbate 20 (or Tween 20), or pluronics. Such buffers include, e.g., phosphate, histidine, imidazole, citrate, acetate, succinate, glutamate, Tris and glycine can be added to keep desirable pH.

In order to minimize the mass that needs to be dissolved during injection, the formulation can be composed mostly by active ingredients. For example, protein or peptide products can be lyophilized with the final solid content of 95% of protein or peptide and 5% of stabilizer.

Pharmaceutical products (active ingredients) contemplated for use include small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. In addition, active ingredients of the present invention can be perceptible. A wide range of active ingredients are contemplated. These include but are not limited to hormones, cytokines, hematopoietic factors, growth factors, antiobesity factors, trophic factors, anti-inflammatory factors, and enzymes One skilled in the art will readily be able to adapt a desired active ingredient to the powdered formulations of present invention.

Active ingredients can include but are not limited to insulin, gastrin, prolactin, human growth hormone (HGH), adrenocorticotropic hormone (ACTH), thyroid stimulating hormone (TSH), luteinizing hormone (LH), follicle stimulating hormone (FSH), human parathyroid hormone (PTH), glucagons-like peptide 1 (GLP-1), growth hormone-releasing factor (GRF), human chorionic gonadotropin (HCG), motilin, interferons (alpha, beta, gamma), interleukins (IL-1 to IL-12), interleukin-1 receptor antagonists (IL-Ira), tumor necrosis factor (TNF), tumor necrosis factor-binding protein (TNF-bp), erythropoietin (EPO), granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), novel erythropoiesis stimulating protein (NESP), bone morphogenetic protein (BMP), superoxide dismutase (SOD), tissue plasminogen activator (TPA), urokinase, streptokinase and kallikrein, and various human antibodies and humanized antibodies. The term proteins, as used herein, includes peptides, polypeptides, consensus molecules, analogs, derivatives or combinations thereof.

In one embodiment of the present invention, the lyophilized formulation comprises a model protein drug substance, recombinant human parathyroid hormone (PTH), with standard excipients, mannitol and phosphate.

Diluent to be used with the powders contained within the container closure assembly can also be customized for the best stability and patient compliance. Diluents contemplated for use include commercially available water for injection (WFI), bacteriostatic water for injection (BWFI), or phosphate buffered saline (PBS), etc. Custom developed diluent can further contain a buffering agent, e.g., acetate, phosphate, histidine, citrate, acetate, succinate, glutamate, and glycine; surfactants; stabilizers; tonicity modifiers like sodium chloride; metal ions; local anesthetic agents like lidocaine or benzyl alcohol, and hydrogels for controlled release, etc.

Materials contemplated for use in the manufacturing of the product container, top cup component, plug component and/or plunger assembly of the present invention include, e.g., cyclo olefin copolymer, polycarbonate, polystyrene, Teflon, and the like. Such materials are well known to those of ordinary skill in the art and readily available.

The product container may vary in size and configuration but is typically cylindrical in shape, and has at one end an opening and at the other end an ejection port. An important, unique design feature of the product container is a spiral mixing channel that is integrated into the product container at the lower base. The spiral mixing channel serves to enhance the recovery of the powder due to fluid path within the container. The product container will be specifically designed to hold a sufficient volume of liquid active ingredient and specifically designed to accept a plunger assembly. At the ejection port end, the product container may be specifically designed to: 1) allow attachment via friction fit to either a luer-lock or luer-slip standard needle; 2) comprise a staked needle (with a needle shield); 3) comprise a nozzle spray tip for nasal delivery; or 4) comprise a blunt tip for oral or ocular applications. In each configuration, the ejection port end of the product container will have a detachable base which serves to hold and stabilize the product container during filling and during the lyophilization process. In addition, the detachable base serves as a needle shield when the ejection port end of the product container comprises a staked needle.

The top cup component may vary in size and configuration and is capable of engaging with the plug component with a snug fit to form a plunger assembly having varying manufacturing and/or end user functionality. The top cup component may comprise a detachable tab seal which, when torqued and detached, allows for attachment via friction fit of the top cup to either a luer-lock or luer-slip syringe. Alternatively, the top cup may comprise a lock-ring cap in place of the tab seal. The top cup component may be specifically designed to comprise one or more fluid transfer channels which allows for diluent from the attached syringe to flow through the plunger assembly and encounter the lyophilized powder in the product container.

The plug component may vary in size and configuration and is capable of engaging with the top cup component with a snug fit to form a plunger assembly having varying manufacturing and/or end user functionality. The plug component will be specifically designed such that when fully engaged with the top cup component to form a plunger assembly, there is minimal fluid head space, i.e., minimal holdup volume of the transfer diluent, and such that when the plunger assembly is fully engaged with the product container the plunger assembly compresses the powdered active ingredient and there is minimal fluid head space. The plug component may be specifically designed to comprise one or more fluid transfer channels which allows for diluent from the attached syringe to flow through the plunger assembly and encounter the lyophilized powder in the product container.

Also contemplated for use in the container closure assembly of the present invention is a one piece plunger assembly specifically designed to be accepted by the product container such that when the plunger assembly is fully engaged with the product container the plunger assembly compresses the powdered active ingredient and there is minimal fluid head space. The one piece plunger assembly will comprise: a detachable tab seal and luer lock tab fitting cavity to allow for friction fit of a standard type luer slip syringe at the top end; a circular cavity that can accommodate a typical luer lock syringe; and a defined fluid transfer channel which facilitates flow of fluid through said plunger assembly.

It is understood that the container closure assembly of the present invention may vary in size and is readily adaptable to and functional with any standard type pre-filled syringe and standard type needles. Such syringes and needles are well known to those of ordinary skill in the art and readily available. Generally, the container physical dimensions should be roughly no more than 25 mm×25 mm×150 mm and the container should have provisions for filling up to 20 ml of liquid pharmaceutical product to be lyophilized.

In the improved process for the preparation of a container closure assembly containing a lyophilized powder product, 1) the empty product container (with detachable base) is loaded into a industry standard vial/syringe/cartridge manufacturing filling line in a similar manner as regular vials, syringes, or cartridges; 2) the product container is filled with an optimized liquid formulation containing a pharmaceutical product; 3) a plunger assembly is dropped into an "open" position on top of the product container, engaging the product container in the same manner as lyophilization stoppers are mounted to regular vials, creating a container closure assembly; 4) the container closure assembly is then placed into the lyophilizer and subjected to a lyophilization process; 5) during lyophilization, vapor escapes via the openings between the plunger assembly and the product container; 6) upon completion of lyophilization, vertical compression of the lyophilizer shelves will push the plunger assembly into the product container creating a sealed container closure assembly and compressing the dry powder to minimal head space; and 7) the sealed container closure assembly is bonded to provide a tamper resistant assembly which retains the sterility of the active ingredient. Importantly, in this process, the plunger assembly is pushed down such that it compresses the pharmaceutical powder and there is minimal air space between the product container and the plunger assembly. This design concept reduces the volume of air, reduces residual drug at the completion of injection, and facilitates the direct injection of the lyophilized powder without the need for a separate reconstitution/mixing/priming step of powder with diluent.

Methods and techniques to be used to bond the sealed assembly are well known to those of ordinary skill in the art and include, e.g., gluing, welding. The bonding serves to help maintain seal integrity and provide a tamper resistant assembly which retains the sterility of the active ingredient. As such, the bonded sealed container closure assembly of the present invention is able to retain the sterility of the pharmaceutical powder product and is storage stable at room temperature over the shelf life of the product.

In the improved method for the administration of a lyophilized pharmaceutical product using the container closure assembly of the present invention, 1) the detachable tab seal on the top of the assembly is removed by applying a tangential force thus exposing the top of the plunger assembly for attachment of a pre-filled syringe containing the diluent; 2) the detachable base located on the opposing ejection port end of the container closure assembly is removed, thus exposing a luer-slip tip for the attachment of a needle; 3) a luer-slip needle is attached via friction fit to the exposed luer-slip tip of the container closure assembly; 4) the injection is then initiated by inserting the needle into the injection site; 5) force is applied to the syringe plunger whereupon the diluent in the syringe will be forced through the plunger assembly; 6) the diluent will be guided through a designed path to encounter the lyophilized powder in the product container and rapidly reconstitute; and 7) the reconstituted liquefied product mixture exits the container closure assembly through the ejection port, passes through the attached needle and into the injection site. As an alternative to steps 2) and 3), the container closure assembly may have a staked needle at the ejection port end, which is exposed when the detachable base is removed. In another embodiment, as an alternative to steps 2) and 3), the container closure assembly may comprise a nozzle spray tip at the ejection port end which is exposed when the detachable base is removed. In yet another embodiment, as an alternative to steps 2) and 3), the container closure assembly may comprise a blunt tip at the ejection port end which is exposed when the detachable base is removed. Importantly, none of the methods described above require a separate reconstitution/mixing/priming step, thereby providing for a more convenient and ease of use for the patient and/or end user.

Importantly, the improved delivery method of the present invention provides a 'gradient delivery' of the injectable pharmaceutical product. For example, because the present invention provides for the immediate reconstitution of the powdered drug upon contact with the diluent, the product is injected into the patient in a manner wherein more highly concentrated product is injected initially. It is the improved process and container closure assembly design concept described herein that facilitates the direct administration of the powdered active ingredient, without the need for a separate reconstitution/mixing step. It is thus envisioned that the lyophilized formulations, lyophilization processes and closure assembly design concepts described herein could be applied to existing delivery devices, e.g., pen systems, auto-injector systems, needle-free injector systems, dual-chambered injection cartridges and/or pre-filled syringe systems, to provide for improved methods of administration of powdered drugs which provide for gradient delivery and which are more user friendly for the patient and/or end user.

EXAMPLE 1

In this Example, a study was conducted to demonstrate the 'gradient delivery' injection profile associated with the administration of a powdered drug using the formulations, lyophilization processes and container closure assembly design of the present invention.

Figure 10:
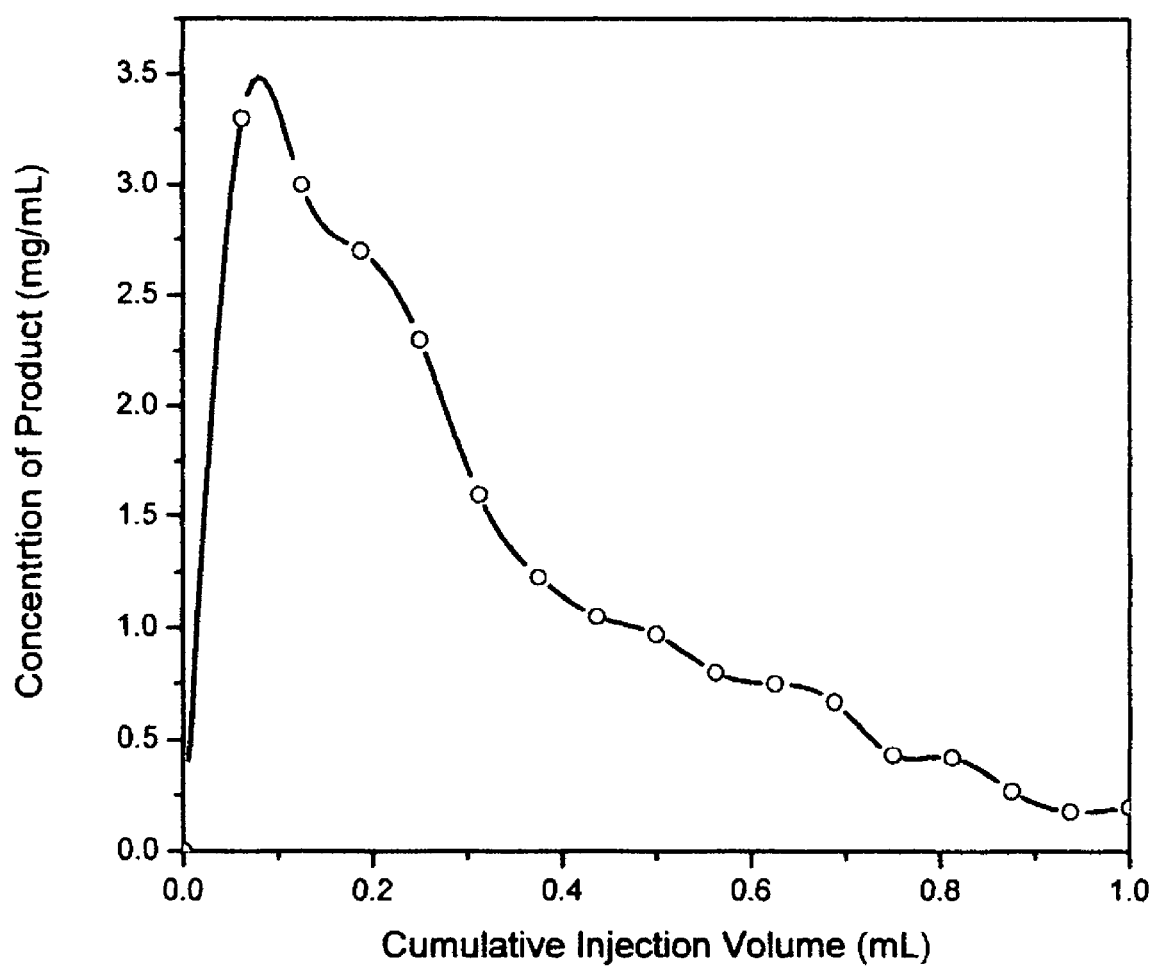
FIG. 10 is a graph depicting the 'gradient delivery' injection profile associated with the administration of a powdered drug using the powder formulations, lyophilization processes, and container closure assembly of the present invention. Protein concentration is plotted versus cumulative injection volume.

The study was performed utilizing a model protein drug substance, Recombinant Human Parathyroid Hormone (PTH) with standard excipients, mannitol and phosphate. The study was performed by using a sealed container closure assembly prepared using the process of the present invention and containing 10 mg of PTH powder which was dried in a typical lyophilization process. A syringe containing 1 ml of diluent (water) was attached to the plunger assembly of the container closure assembly and the detachable base at the neck end of the container closure assembly was removed. Force is applied to the syringe plunger such that the water flows through the assembly, reconstitutes the powder, and the resultant solution drips out of the ejection port of the assembly. The concentration of PTH in each drop of solution was measured with a ultraviolet spectrometer. The data collected and shown in FIG. 10 characterize the general profile of the gradient delivery associated with the administration of a powdered drug using the formulations, lyophilization processes and container closure assembly design of the present invention. As depicted in FIG. 10, the concentration of the dose delivered over the injection volume for a gradient delivery is non constant with the bulk of the active pharmaceutical ingredient being delivered during the initial portion of the injection.

Figure 11:
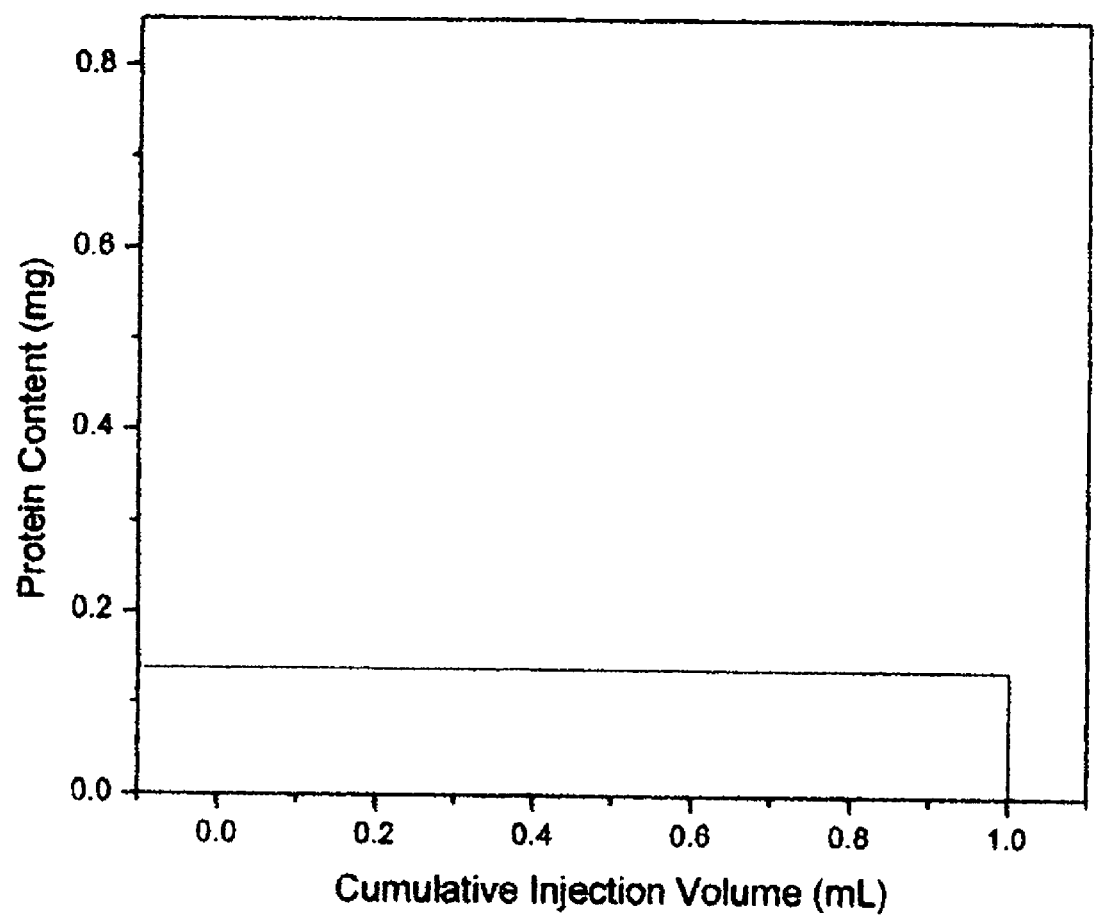
FIG. 11 is a graph depicting an injection profile representative of those associated with the administration of a powdered drug using prior art devices which require a reconstitution and/or mixing step of the powdered drug with a diluent prior to injection. Protein concentration is plotted versus cumulative injection volume.

This unique gradient delivery of the injectable pharmaceutical powder product may be advantageous to the patient in certain therapeutic settings. To date, none of the known prior art delivery techniques and devices used for delivery of powdered drugs have such a profile, as all require a reconstitution and/or mixing step of the powdered drug with a diluent prior to injection, and therefore have an injection profile similar to that depicted in FIG. 11. Although this specific protein was used, it is highly probable that for those skilled in the art and for most standard active pharmaceutical products, excipients and other ingredients that the same results can be achieved and will reflect these same characteristics and injection response.

The improved lyophilized formulations, lyophilization processes and closure assembly design concepts of the present invention provide patients and end-users with an alternative, less expensive and easier to use device than current state-of-the-art delivery systems for lyophilized products. Utilization of the design concept described for container closure assembly of the present invention on existing delivery devices would provide a valuable and much needed benefit to those patients dependent upon powdered drugs in their therapeutic settings.

What is claimed is:

1. A container closure assembly suitable for lyophilized pharmaceutical products comprising:
   a plunger assembly comprising:
      a luer lock tab fitting cavity to allow for friction fit of a standard type luer slip syringe;
      a circular cavity that can accommodate a typical luer lock syringe; and
      a defined fluid transfer channel extending axially from the proximal end to the distal end of a plug component which facilitates flow of fluid through said assembled plunger assembly; wherein said fluid transfer channel is on the outside of the plug compartment and
   a product container component comprising:
      an open end having a chamber capable of holding a liquid active ingredient to be lyophilized and designed to accept said plunger assembly;
      a locking ridge integrated into the sidewall of said product container;
      an opposing lower base comprising a coaxial hollow ejection port; and
      a spiral mixing channel integrated into said lower base.

2. A container closure assembly suitable for lyophilized pharmaceutical products comprising:
   a plug component comprising:
      a defined fluid transfer channel extending axially from the proximal end to the distal end on the outside of the plug component which allows for flow of fluid through said plug component;
   a top cup component comprising:
      a luer lock tab fitting cavity to allow for friction fit of a standard type luer slip syringe;
      a circular cavity that can accommodate a typical luer lock syringe;
      a hollow circular inside capable of accepting said plug component to create a plunger assembly; and
   a product container component comprising:

an open end having a chamber capable of holding a liquid active ingredient to be lyophilized and designed to accept said plunger assembly;

a locking ridge integrated into the sidewall of said product container;

an opposing lower base comprising a coaxial hollow ejection port; and a spiral mixing channel integrated into said lower base.

* * * * *